US00PP33780P2

(12) United States Plant Patent
O'Connell

(10) Patent No.: US PP33,780 P2
(45) Date of Patent: Dec. 21, 2021

(54) ***SEDUM* 'SHOOTING STARS'**

(50) Latin Name: *Sedum adolphi*
Varietal Denomination: SHOOTING STARS

(71) Applicant: Altman Specialty Plants, Inc, Vista, CA (US)

(72) Inventor: Renee O'Connell, Escondido, CA (US)

(73) Assignee: Altman Specialty Plants Inc., Vista, CA (US)

( * ) Notice: Subject to any disclaimer, the term of this patent is extended or adjusted under 35 U.S.C. 154(b) by 0 days.

(21) Appl. No.: 17/091,502

(22) Filed: Nov. 6, 2020

(51) Int. Cl.
*A01H 5/00* (2018.01)
*A01H 6/32* (2018.01)

(52) U.S. Cl.
USPC ..... Plt./479

(58) Field of Classification Search
USPC ..... Plt./479
See application file for complete search history.

*Primary Examiner* — Annette H Para
(74) *Attorney, Agent, or Firm* — Cassandra Bright

(57) ABSTRACT

A new and distinct cultivar of *Sedum* plant named 'Shooting Stars' is disclosed, characterized by yellow-green foliage with a strong fiery orange marginal flush. Plants are dwarf with abundant branches and foliage, creating a brightly colored, full plant. The dwarf plants are suitable for fairy gardens and other small garden uses, and grow robustly. The new variety is a *Sedum*, typically be produced as a container plant for the patio or as landscape plants, as well as a variety of ornamental purposes.

2 Drawing Sheets

Figure 1:
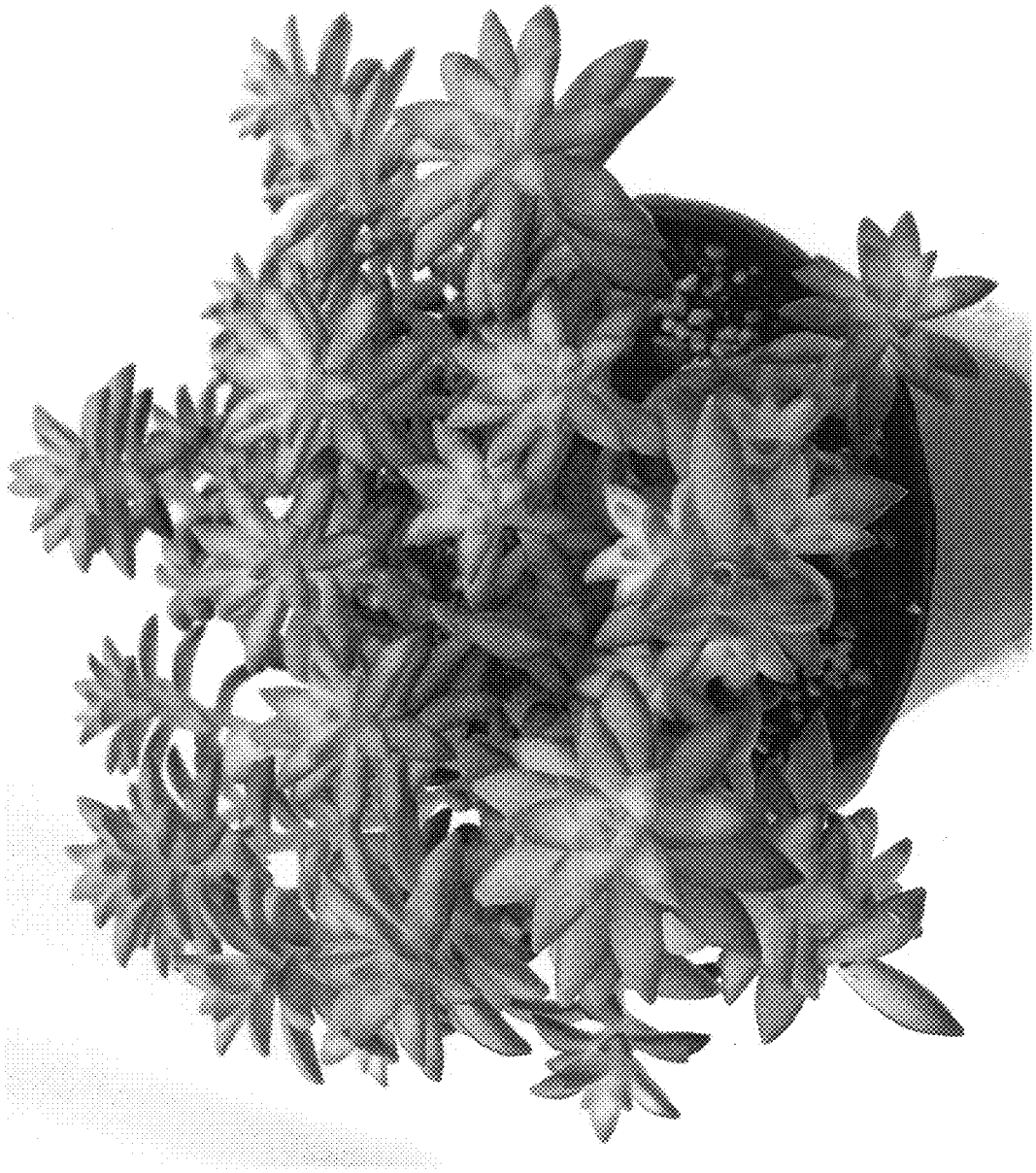

Latin name of the genus and species: *Sedum adolphi.*
Variety denomination: 'SHOOTING STARS'.

BACKGROUND OF THE INVENTION

The new cultivar, *Sedum* 'SHOOTING STARS', is the product of chance discovery. The new variety originated as a naturally occurring whole plant mutation of the parent, *Sedum* 'Firestorm' (unpatented). The new cultivar 'SHOOTING STARS' was discovered by the inventor, Renee O'Connell, in June 2017, in Vista, Calif., at a commercial greenhouse.

*Sedum* Asexual reproduction of the new cultivar 'SHOOTING STARS' was first performed September 2017 in Vista, Calif., at a commercial greenhouse, by terminal vegetative cuttings. *Sedum* 'SHOOTING STARS' has since produced multiple generations and has shown that the unique features of this cultivar are stable and reproduced true to type.

SUMMARY OF THE INVENTION

The cultivar 'SHOOTING STARS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SHOOTING STARS'. These characteristics in combination distinguish 'SHOOTING STARS' as a new and distinct *Sedum* cultivar:

1. *Sedum adolphi* 'Shooting Stars' is a miniature sport of *Sedum adolphi* 'Firestorm', exhibiting all of the fiery orange color in bright light as *Sedum adolphi* 'Firestorm', but with a more miniature morphology.

2. *Sedum adolphi* 'Shooting Stars' branches prolifically, creating a cluster quickly.
3. *Sedum adolphi* 'Shooting Stars', due to its inherently small morphology, and bright tangerine orange color, offers a colorful option for fairy gardens or other small gardens.
4. *Sedum adolphi* 'Shooting Stars' forms branches that seem to have an extra amount of leaves, as compared to *Sedum adolphi* 'Firestorm', creating stem rosette that is fuller in appearance.
5. *Sedum adolphi* 'Shooting Stars' shows the same robust growth without cultural problems as does *Sedum adolphi* 'Firestorm'.

PARENTAL COMPARISON

Plants of the new cultivar are similar to plants of the parent, in most horticultural characteristics, however, plants of the new cultivar differ in the following;

1. *Sedum adolphi* 'Shooting Stars' forms plants that are much smaller than *Sedum adolphi* 'Firestorm'.
2. *Sedum adolphi* 'Shooting Stars' produces stem rosettes with more leaves, creating a a stem rosette more full in appearance than that of *Sedum adolphi* 'Firestorm'.
3. *Sedum adolphi* 'Shooting Stars' produces leaves that are somewhat flatter than those of *Sedum adolphi* 'Firestorm'.
4. *Sedum adolphi* 'Shooting Stars' appears to have a narrow red orange outline on the margin of each leaf, whereas *Sedum adolphi* 'Firestorm' is margined with solid orange.
5. *Sedum adolphi* 'Shooting Stars' exhibits a similar robust growth as does *Sedum adolphi* 'Firestorm'.

COMMERCIAL COMPARISON

The new cultivar 'Shooting Stars' can be compared to the unpatented, unnamed commercial variety *Sedum adolphi* found in horticultural commerce. Plants of the commercially grown *Sedum adolphi* are similar to plants of the new cultivar 'Shooting Stars' in most horticultural characteristics. However, the new cultivar 'Shooting Stars' differs in the following:

1. *Sedum adolphi* 'Shooting Stars' produces a morphologically smaller plant.
2. *Sedum adolphi* 'Shooting Stars' displays leaves that are tangerine orange, with red lineal margins, whereas the commercial *Sedum adolphi* exhibits leaves that vary from golden to a duller orange color.
3. *Sedum adolphi* 'Shooting Stars' exhibits more leaves in the rosette, resulting in a fuller appearing rosette.
4. *Sedum adolphi* 'Shooting Stars' can be used in fairy gardens and other pot sizes requiring plants with small morphologies, whereas the commercial *Sedum adolph* is typically used for quarts and gallons for planting in the landscape.

The new cultivar 'Shooting Stars' can be compared to the unpatented commercial variety *Sedum* 'California Sunset'. Plants of *Sedum* 'California Sunset' are similar to plants of the new cultivar 'Shooting Stars' in most horticultural characteristics. However, plants of the new cultivar 'Shooting Stars' differ in the following:

1. *Sedum adolphi* 'Shooting Stars' produces morphologically smaller plant than does *Graptosedum* 'California Sunset'
2. *Sedum adolphi* 'Shooting Stars' displays leaves that are tangerine, with a lineal margin of red, whereas *Graptosedum* 'California Sunset' produces leaves that are blue-green at times, and peach-rose at other times of the year.
3. *Sedum adolphi* 'Shooting Stars', due to its smaller morphology, can be successfully used in small pots such as 2.5", 72 cell and fairy gardens or other small gardens, still giving the appearance of a "mature" plant, whereas *Graptosedum* 'California Sunset' is best utilized in a quart or gallon size for planting in the landscape.
4. *Graptosedum* 'California Sunset' does not display lineal leaf margin in red, whereas *Sedum adolphi* 'Shooting Stars' exemplifies this characteristic.

BRIEF DESCRIPTION OF THE PHOTOGRAPHS

The accompanying photograph in FIG. 1 illustrates in full color a typical plant of 'SHOOTING STARS' grown in a greenhouse in Vista, Calif. (approximately 3500 foot candles).

Figure 2:
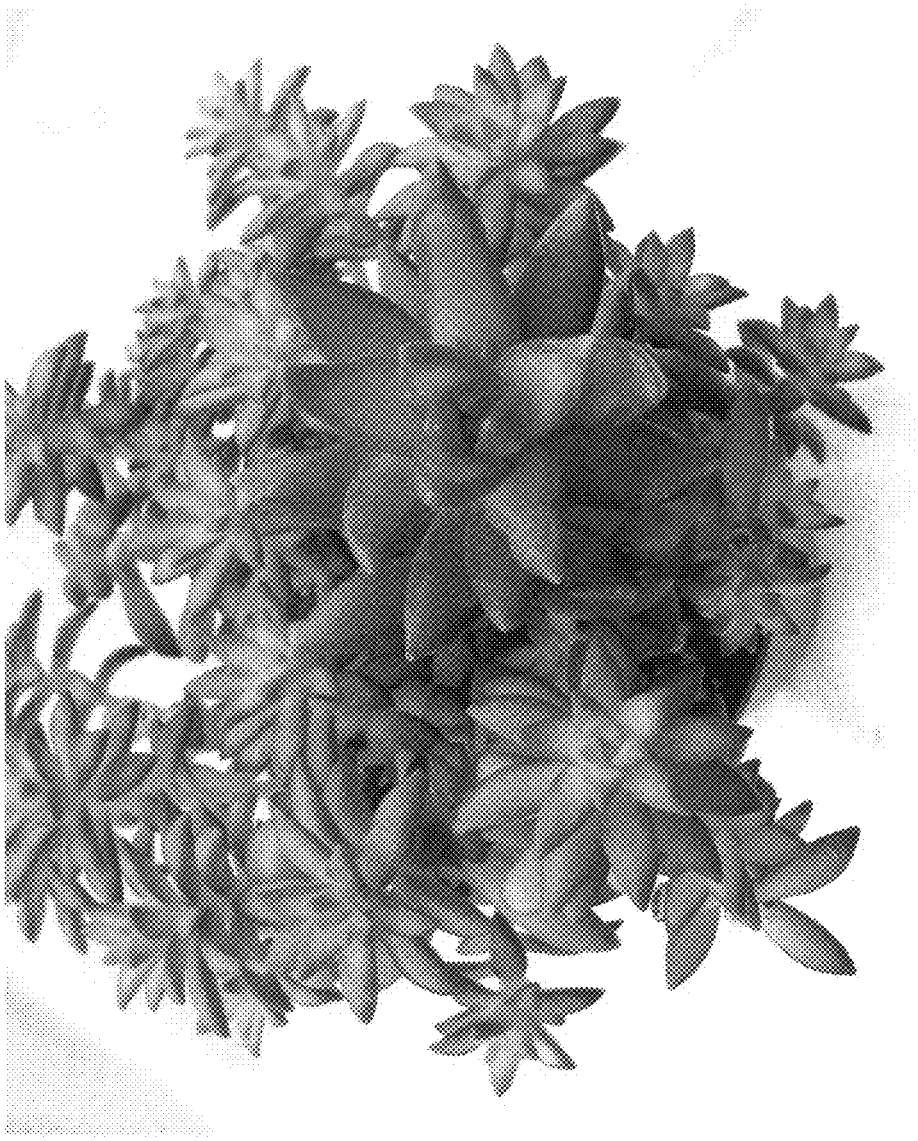

FIG. 2 illustrates a plant of the new variety 'SHOOTING with a cutting of the parent variety *Sedum* 'Firestorm' set within the plant for size comparison.

The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Sedum* plant. Temperatures ranged from 2° C. to 29° C. night and day. No artificial light, photoperiodic treatments or chemical treatments were given to the plants.

DETAILED BOTANICAL DESCRIPTION

In the following description, color references are made to The Royal Horticultural Society Colour Chart, 2007 except where general terms of ordinary dictionary significance are used. The following observations and measurements describe 'Shooting Stars' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 fc of light. Measurements and numerical values represent averages of typical plant types.

Botanical classification: *Sedum* hybrid 'SHOOTING STARS'.

PROPAGATION

Type of propagation typically used: Terminal vegetative cuttings.

Time to initiate roots: About 10 days at approximately 24° C.

Root description: Fibrous.

PLANT

Age of plant described: Approximately 4 months from a cutting.

Container size of the plant described: 1 gallon.

Growth habit: Semi-upright succulent. Starts upright, then trails.

Height: Approximately 12 to 14 cm.

Plant spread: Approximately 22 to 28 cm.

Vigor: Robust.

Branching characteristics: Basal occurring main branches. Abundant sub-opposite lateral branches.

*Length*.—Main branches about 10 cm to 15 cm, lateral branches about 5 cm to 8 cm.

*Width*.—5 to 7 mm.

*Color*.—Near Yellow-Green 145C.

*Texture*.—Glabrous.

*Appearance*.—Shiny.

*Strength*.—Moderately strong.

*Internode*.—About 1.0 cm.

FOLIAGE

Arrangement: Sub-opposite, forming dense, evenly spaced rosettes.

Foliar internode: About 2 mm.

Average length: Mature foliage average range 2.5 cm to 3.2 cm.

Average width: 7 to 9 mm.

Width at base: 3 mm.

Center (deepest) depth: 6 mm.

Shape of blade: Oblong.

Apex: Acute.

Base: Truncate.

Margin: Entire.

Texture of top surface: Glabrous.

Texture of bottom surface: Glabrous.

Appearance of top surface: Moderately shiny.

Appearance of top surface: Slightly shiny.

Quantity: Average of 70 on one main branch having 6 lateral branches.

Color:

*Young foliage upper side*.—Near Yellow-Green 145C, apex Greyed-Red 178C flushed Orange-Red 34A.

*Young foliage under side*.—Near Yellow-Green 145C, apex Greyed-Red 178C.

*Mature foliage upper side*.—Near Greyed-Red 178B, flushed Orange-Red 34A. Base and central streak near Yellow-Green 145C.

*Mature foliage under side*.—Near Yellow-Green 145C apex Greyed-Red 178B, flushed Orange-Red 34A.

Venation: Indistinguishable from leaf blade.

FLOWER

Not observed.

REPRODUCTIVE ORGANS

Not observed.

OTHER CHARACTERISTICS

Fruits and seeds: Not observed.

Temperature tolerance: Tolerates temperatures from approximately 0° C. to at least 32° C.

Disease/pest resistance: Neither resistance or susceptibility to other normal diseases and pests of *Sedum* has been observed.

Drought tolerance: Tolerates at least 2 weeks of high temperatures without supplemental water, showing no serious damage to plant.

What is claimed is:

1. A new and distinct cultivar of *Sedum* plant named 'SHOOTING STARS' as herein illustrated and described.

* * * * *